United States Patent [19]
Allison

[11] Patent Number: 4,531,945
[45] Date of Patent: Jul. 30, 1985

[54] MULTI LAYER SANITARY APPLIANCE

[75] Inventor: John P. Allison, Outagamie County, Wis.

[73] Assignee: Kimberly-Clark Corporation, Neenah, Wis.

[21] Appl. No.: 546,769

[22] Filed: Oct. 31, 1983

[51] Int. Cl.³ .............................................. A61F 13/16
[52] U.S. Cl. .................................. 604/378; 604/382; 428/74; 428/284
[58] Field of Search ................ 604/378, 382; 428/287

[56] References Cited
U.S. PATENT DOCUMENTS

| | | | |
|---|---|---|---|
| 3,699,966 | 10/1972 | Chapuis | 604/378 X |
| 3,825,006 | 7/1974 | Ralph | 604/378 X |
| 3,936,555 | 2/1976 | Smith, II | 428/287 X |
| 4,357,939 | 11/1982 | Jackson et al. | 604/378 X |
| 4,372,312 | 2/1983 | Fendler et al. | 604/378 X |
| 4,411,660 | 10/1983 | Dawn et al. | 604/378 X |
| 4,413,996 | 11/1983 | Taylor | 604/382 |

Primary Examiner—George F. Lesmes
Assistant Examiner—Nancy A. B. Swisher

[57] ABSTRACT

A sanitary appliance such as a sanitary napkin is provided with at least three layers of absorbent material with the first and third layer being substantially identical and having areas of contact through at least one opening in the second layer.

4 Claims, 1 Drawing Figure

MULTI LAYER SANITARY APPLIANCE

FIELD OF THE INVENTION

This invention relates to a secretafacient article, e.g., a sanitary napkin and particularly to such an article having a multi-layer absorbent system.

BACKGROUND OF THE INVENTION

Recently, sanitary appliances such as sanitary napkins have been introduced with multiple layers of absorbent material. An example of such a napkin is one sold under the trademark NEW FREEDOM Maxi Thin by Kimberly-Clark Corporation, Neenah, Wis. There are advantages to sanitary appliances having multilayer absorbent systems. One of the principle advantages is the ability to design each of the layers of the absorbent to fit particularly desirable product attributes. For example, it is known to be desirable to isolate absorbed fluid from the body surface of the wearer (or user) of a sanitary appliance. It is also desirable to increase the resilience and flexibility of these sanitary appliances to more closely conform to body movements. These goals are accomplished in multilayer pads, at least in part, by having an absorbent layer with relatively large capillaries as the absorbent surface nearest the body of the wearer while utilizing a second absorbent layer of substantially smaller capillaries under the first layer. One of the methods of obtaining an absorbent layer with large capillaries is to form such a layer with relatively large denier thermoplastic fibers alone or in combination with other traditionally absorbent cellulosic fibers as the base for the top layer. U.S. Pat. Nos. 4,082,886; 4,129,132; 3,976,074; 4,054,141; 4,047,531; 3,545,441; and 4,219,024 are representative patents describing the use of thermoplastic fibers in some instances in conjunction with other fibers to form an absorbent web with large capillaries in a multi-component absorbent system.

As the percentage of thermoplastic fibers increase in this upper layer, the amount of fluid retained during use decreases because of the inherent hydrophobicity of these fibers. When the upper layer is made up of a 100% thermoplastic fibers, fluid present in the layer may be easily expelled when subjected to compaction forces. However, for purposes of this invention, the term absorbent layer is meant to include such layers although, they do not function as an absorbent in the traditional sense.

In order to provide a sanitary appliance with a dry surface on the area adjacent the wearer, fluid must be transported rapidly downward away from the wearer and there must be some driving force to provide for this downward, i.e., z direction transfer. While in many instances, gravity provides some of the force necessary for z direction transfer, in the case of viscous fluids, particularly blood and menses, the fluid tends to stay on the surface of the sanitary appliance. In this instance, the difference between the capillary size gradients of the first and second absorbent layer should be as great as practicable. The smaller the capillary size the greater the attraction for fluid and, with regard to the second absorbent layer, the more z direction force which is exerted on the fluid. With regard to the characteristics of the first layer, the larger the capillaries, the less the fluid retention and the more efficient the z direction transfer into the second layer.

U.S. Pat. No. 4,397,644 issued to B. J. Matthews et al describes an absorbent system employing these principles and also localized densified zones in the upper absorbent layer to provide preferential conduit sites for downward transfer due to their reduced capillary size compared to the other portions of this layer.

An effective primary absorbent layer for this system is a surfactant treated meltblown microfiber web described in U.S. Pat. No. 4,372,312 which provides a layer of superior absorbent wicking. This layer is particularly effective when superabsorbent particles or small fibers are entrapped throughout the web. This combination is most efficient when the individual superabsorbent particles or fibers are widely spaced throughout the web. This combination is described e.g. in British application No. 8233488. (Wicking is defined as fluid migration along a surface from the point of initial contact of the fluid.) When an absorbent layer has extremely small capillaries such as the meltblown microfiber and when the capillary structure of the absorbent layer positioned between the wearer and the small capillary absorbent layer has very large capillaries and is extremely thin or when the densified zones are particularly efficient in fluid transfer (as described in the Matthews et al patent hereby incorporated by reference), the rapid influx of the large volume of fluid may overwhelm the system to the extent that the rate of wicking is lower than the rate of fluid discharge on the top surface of the small capillaried absorbent. When this occurs, the small capillary absorbent layer functions as a dam with the fluid backing up into the upper absorbent layer from which will ultimately produce spreading of the stain throughout the upper layer and on the cover material and may actually expel the fluid in some circumstances.

One of the ways to increase the rate of z direction fluid transfer is to eliminate sections of the first absorbent layer entirely. U.S. Pat. Nos. 4,055,180; 3,593,717; 4,342,314; 4,173,046; and British Pat. No. 2,055,586 teach the use of holes either in the cover or in an upper absorbent layer to provide for this increased z direction transfer. This approach does not solve the damming problem associated with the second small capillary-containing layer, however.

The ideal system, therefore, is one which provides for rapid z direction transfer but at a rate which does not overwhelm the horizontal wicking capabilities of the second small capillary-containing layer.

SUMMARY OF THE INVENTION

According to this invention a secretafacient article having a multilayer absorbent system is provided in which the absorbent system has at least three layers with the first layer being substantially identical in capillary size and the second layer having substantially smaller capillaries than the other absorbent layers and composition to the third layer. These two layers are in contact through at least one space provided in the second layer. The space is generally positioned under the general area of fluid discharge in the zone in the first layer through which the fluid generally migrates downward (as used above, area refers to the portion on the surface of the secretafacient article, e.g., napkin and zone refers to the volume of the first absorbent layer through which fluid migrates generally positioned beneath the perineal area of the napkin. In the case of a sanitary napkin the area is at least about one centimeter wide and five centimeters in length. While the fluid will migrate downward based upon its initial spread on the surface of a sanitary napkin this 1×5 cc. area generally describes that portion adjacent the perineal area where all of the fluid will be initially discharged and directed if the cover of the napkin is effective.

By having a space in which the first and third layer contact each other of a sufficient size to allow the zone to be extended into or near the third layer, the fluid will wick along the bottom surface of the small-capillaried second layer as well as the top surface thereby effectively doubling the useable surface for wicking and its rate of fluid uptake. This fluid transfer from first to third layer can only be assured by actual contact of these layers through space within the second layer sufficient to allow fluid transport in the z direction into the third layer generally beneath the perineal area.

While this invention has application most particularly in the area of sanitary napkins, it may also be utilized for any secretafacient article. Secretafacient being defined as an article which efficiently absorbs bodily fluids either menses, urine, or discharges from wounds. The advantages accruing to this absorbent system do, however, have much more substantial effect when the fluid to be absorbed is a viscous one as opposed to comparatively nonviscous fluids such as urine.

A presently preferred second absorbent layer useful for the secretafacient of this invention is one which employs surfactant treated meltblown microfiber which may contain isolated super absorbent particles entrapped within. The first and third layer is preferably made of substantially 100% thermoplastic fiber preferably of large diameter to provide for maximum fluid transport in the z direction due to the result of large capillaries. The fibers should be between about 1.5-15 denier and 3-6 denier for the currently preferred optimum fibrous web. If some level of fluid retention is desired in the top layer at the risk of decreasing the rapidity of fluid transfer in the z direction, a turbulently airlaid mixture of microfiber and wood pulp fiber such as described in U.S. Pat. No. 4,100,324 may be used. If this coformed material is used it is preferred that a substantial proportion of the mixture be meltblown microfiber to prevent the inherent collapse of capillaries resulting from the wetting of cellulosic material.

Figure 1:
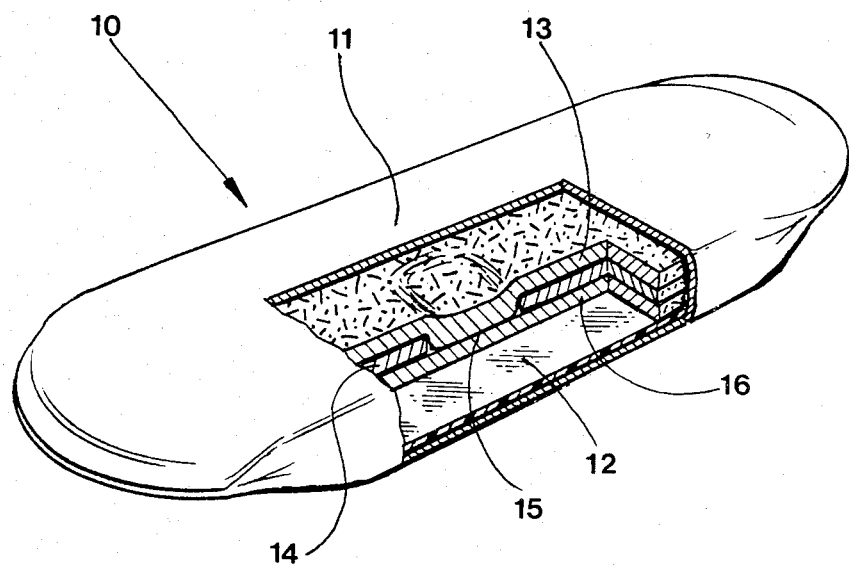
FIG. 1 is a perspective view of a sanitary napkin partially in cross-section made in accordance with the teachings of this invention. As can be seen from FIG. 1, sanitary napkin 10 has an outer wrap 11 which extends completely around the other components of the sanitary napkin overlying the bottom of wrap 11 designed to be positioned between the absorbent layers 13, 14, and 16 is fluid impermeable baffle 12.

The absorbent system of this particular embodiment of a sanitary napkin according to this invention employs a meltblown microfiber layer 14 positioned between alternate layers 13 and 16 made of the coformed airlaid mixture of materials described previously. In the approximate center of the napkin corresponding to the perineal area of the wearer, layers 13 and 16 abut each other through an opening in the meltblown microfiber layer 14. This opening need not correspond exactly with the area of discharge on the top of the napkin. This is true because the cross and machine direction wicking associated with the meltblown microfiber will conduct fluid rapidly into this opening. Fluid will then travel downward through this opening in the microfiber layer 14 and wick along the bottom surface of the meltblown microfiber in either direction from the opening. This essentially simultaneous utilization of both surfaces of the small capillary portion of the absorbent system virtually eliminates any possible damming effect due to the relatively large differential in capillary size between the absorbent layer 13 and the small capillary containing absorbent layer 14.

Teachings of this invention are also particularly applicable to the absorbent system taught in U.S. Pat. No. 4,397,644 referred to earlier in which a sanitary napkin with an absorbent system containing a small capillaried absorbent layer positioned under a first absorbent layer with larger capillaries, but with densified zones of smaller capillaries to promote positional z direction transfer. This particular patent contemplates the use of a small capillaried absorbent layer, which may be fluff, used with this transfer zone concept in which, within the transfer zones in an upper generally large capillary absorbent layer downward extending zones produce capillaries of a size essentially equal to that of the small capillary layer thus providing directional pads for fluid migration, the fluid preferring the small capillary zones in the upper absorbent layer. In the case of the upper absorbent layer of the Matthews et al invention the average capillary size of this layer is greater than the second small capillary size layer even though the localized densified zones may have capillaries of the same size. The concept of this invention does in fact contemplate the system described in the Matthews et al invention and fluid transfer is in effect best when one of the transfer zones is directly over or adjacent the spaced area 15 as depicted in FIG. 1. While this invention has generally been described with reference to a sanitary napkin obviously any viscous fluid such as blood can be transferred more effectively according to the arrangement of this absorbent system. Less viscous fluid such as urine can also be transferred effectively by utilizing this absorbent system although the fluid directional effect is not as great and the problems associated with damming are less likely to occur with a less viscous fluid.

What is claimed is:

1. A secretafacient article comprising in combination;
   (a) a fluid pervious cover
   (b) a fluid impermeable baffle
   (c) an absorbent system with at least three substantially coextensive layers including
      (1) a first absorbent layer with relatively large capillaries with a top surface adjacent said cover and a bottom surface, said first absorbent layer including a zone through which fluid generally migrates downward; and
      (2) a second absorbent layer with relatively small capillaries and a top surface adjacent the bottom surface of said first absorbent layer; said second layer having a bottom surface and at least one opening through said top and bottom surfaces beneath said zone in said first layer; and
      (3) a third layer similar in capiliary size to said first layer with a top surface adjacent said bottom surface of said second layer and a bottom surface near said baffle, said top surface in contact with said bottom surface of said first layer through said at least one opening in said second layer.

2. The article according to claim 1 wherein the second layer comprises surfactant treated meltblown microfiber.

3. The secretafacient according to claim 1 wherein the first and third layer are formed from a turbulently airlaid mixture of meltblown microfiber and woodpulp fibers.

4. The article according to claim 2 or 3 wherein the second layer contains spacedly entrapped superabsorbent material.

* * * * *